(12) United States Patent
Tagawa et al.

(10) Patent No.: US 10,058,299 B2
(45) Date of Patent: Aug. 28, 2018

(54) RADIATION IMAGING SYSTEM AND RADIOGRAPHY SYSTEM

(71) Applicant: CANON KABUSHIKI KAISHA, Tokyo (JP)

(72) Inventors: Motoki Tagawa, Chigasaki (JP); Akiya Nakayama, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 143 days.

(21) Appl. No.: 15/077,565

(22) Filed: Mar. 22, 2016

(65) Prior Publication Data

US 2016/0278722 A1 Sep. 29, 2016

(30) Foreign Application Priority Data

Mar. 24, 2015 (JP) .................. 2015-061690

(51) Int. Cl.
*A61B 6/00* (2006.01)
(52) U.S. Cl.
CPC .............. *A61B 6/463* (2013.01); *A61B 6/465* (2013.01); *A61B 6/5241* (2013.01); *A61B 6/587* (2013.01); *A61B 6/4233* (2013.01); *A61B 6/4291* (2013.01)
(58) Field of Classification Search
CPC .... A61B 6/4233; A61B 6/4266; A61B 6/5241
See application file for complete search history.

(56) References Cited

U.S. PATENT DOCUMENTS

| 6,273,606 B1* | 8/2001 | Dewaele | A61B 6/5241 378/174 |
| 2011/0049343 A1* | 3/2011 | Yamaguchi | A61B 6/5241 250/252.1 |
| 2011/0110497 A1* | 5/2011 | Nishino | A61B 6/04 378/98.8 |

FOREIGN PATENT DOCUMENTS

| JP | 11-244270 A | 9/1999 |
| JP | 2012-040140 A | 3/2012 |

* cited by examiner

*Primary Examiner* — Hoon Song
(74) *Attorney, Agent, or Firm* — Canon U.S.A., Inc. IP Division (57) ABSTRACT

In a radiation imaging system, which obtains a radiation image of an object based on a plurality of image signals, includes a radiation imaging apparatus, which includes a plurality of pixels arranged in a two-dimensional matrix, configured to convert an irradiated radiation transmitted through an object into an image signal serving as a partial image of the object. In the radiation imaging system, a holding unit for holding the radiation imaging apparatus holds the radiation imaging apparatus to be movable in a direction intersecting a direction in which positions to obtain a plurality of partial images are arranged.

20 Claims, 10 Drawing Sheets

RADIATION IMAGING SYSTEM AND RADIOGRAPHY SYSTEM

BACKGROUND OF THE INVENTION

Field of the Invention

The present invention relates to a radiation imaging system and a radiography system applied to a medical image diagnosis apparatus, a nondestructive inspection apparatus, and an analyzing apparatus using radiations.

Description of the Related Art

There has recently been a demand for imaging of a long observation area (hereinafter, referred to as long-length imaging). Examples in a medical field include imaging the spinal cord, the entire lower limbs, and the whole body to find out a distortion or abnormality of a subject's body. In particular, a radiation imaging system that can perform long-length imaging (i.e., stitch imaging) by one radiation irradiation may be desirable for reducing the subject's body movements and the amount of exposure, as compared to a configuration in which long-length imaging is performed by dividing the observation area into a plurality of sections and performing radiation irradiation a plurality of times.

Japanese Patent Application Laid-Open No. 2012-040140 discusses a radiation imaging system in which a plurality of radiation imaging apparatuses is arranged in a row in a longitudinal direction of long-length imaging so that the radiation imaging apparatuses spatially overlap with each other as seen from a radiation irradiation side. Such a radiation imaging system can perform long-length imaging by one radiation exposure. Japanese Patent Application Laid-Open No. 11-244270 discusses a support member for arranging radiation imaging apparatuses so that the radiation imaging apparatuses spatially overlap with each other as seen from a radiation irradiation side.

However, neither of Japanese Patent Application Laid-Open Nos. 2012-040140 nor 11-244270 discusses how to hold the positions of the radiation imaging apparatuses in a transverse direction orthogonal to the longitudinal direction. In some configurations, the observation area may have an insufficient width in the transverse direction. For example, when a subject with a hump back is imaged from a side, the width of the observation area in the transverse direction may be insufficient depending on the sizes and holding positions of the radiation imaging apparatuses.

SUMMARY OF THE INVENTION

According to an aspect of the present invention, a radiation imaging system including a radiation imaging apparatus configured to convert an irradiated radiation transmitted through an object into an image signal serving as a partial image of the object, the radiation imaging apparatus including a plurality of pixels arranged in a two-dimensional matrix, the radiation imaging system being configured to obtain a radiation image of the object based on a plurality of image signals, includes a holding unit configured to hold the radiation imaging apparatus movably in a direction intersecting a direction in which positions to obtain a plurality of partial images are arranged.

Further features of the present invention will become apparent from the following description of exemplary embodiments with reference to the attached drawings.

DESCRIPTION OF THE EMBODIMENTS

Exemplary embodiments of the present invention will be specifically described below with reference to the accompanying drawings. Details of dimensions and structures described according to the exemplary embodiments are not limited to those described in the following description and illustrated in the drawings. In the present specification, radiations include not only X-rays but also $\alpha$ rays, $\beta$ rays, $\gamma$ rays, particle beams, and cosmic rays.

Figure 1A:
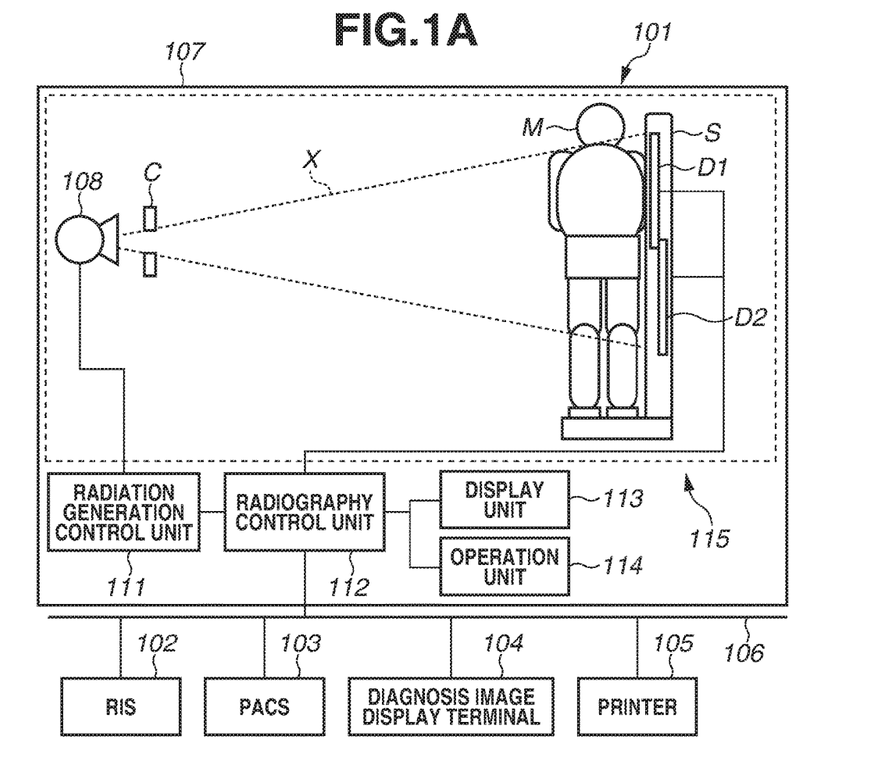
FIGS. 1A and 1B are schematic diagrams illustrating a radiation imaging system according to an exemplary embodiment of the present invention.
Figure 1B:
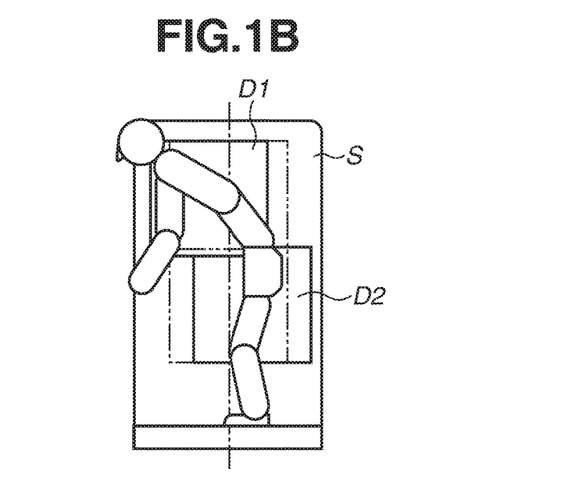

First, a medical diagnosis system will be described with reference to FIGS. 1A and 1B. FIGS. 1A and 1B are schematic sectional views illustrating the medical diagnosis system.

A medical diagnosis system 101 includes a radiology information system (RIS) 102, a picture archiving and communication system (PACS) 103, a diagnosis image display terminal 104, a printer 105, and a radiography system 107. Such apparatuses are connected via a communication means 106 such as a network.

The RIS 102 is a system that manages reservations for inspection and treatment by radiation apparatuses to inspection results. Examples of the system may include an information management system that collectively manages additional information attached to radiation images or inspection orders. The additional information may include inspection information including an inspection identifier (ID) or a reception number. An operator can input an inspection order (inspection instruction) via the RIS 102. According to the inspection order, the radiography system 107 performs imaging. In the present exemplary embodiment, the input inspection order is stored and managed by the RIS 102. However, the input inspection order may be stored and managed by a server (not illustrated) that is connected to the RIS 102 and the radiography system 107. In another exemplary embodiment, the input inspection order may be stored and managed by the radiography system 107.

The PACS 103 stores and manages radiation digital images (hereinafter, referred to as captured images) captured by the radiography system 107. Thus, the PACS 103 can function as part of an image management system that manages captured images. The diagnosis image display terminal 104 can display the captured images stored in the PACS 103, as an output. The printer 105 can print the captured images stored in the PACS 103 as an output.

The radiography system 107 performs inspection (imaging) based on an inspection order including a plurality of pieces of inspection information. The inspection information includes imaging protocol information. Each imaging protocol defines an imaging condition or contents of image processing to be applied to a captured image. More specifically, an imaging protocol includes parameter information or imaging implementation information for use at a time of imaging or image processing, and imaging environment information such as a sensor type and an imaging orientation. The inspection information includes information for identifying an inspection order or identifying a captured image according to an inspection order. Examples of such information include an inspection ID and a reception number.

The radiography system 107 includes a radiation imaging system S, a radiation source 108, a radiation generation control unit 111, a radiography control unit 112, a display unit 113, and an operation unit 114. The radiation imaging system S includes radiation imaging apparatuses D1 and D2. In other words, the radiation imaging system S includes a plurality of radiation imaging apparatuses. The radiation source 108 functions as a radiation generation unit. More specifically, the radiation source 108 in the present exemplary embodiment is an X-ray tube. The radiation source 108 emits radiations (here, X-rays) toward an object (subject). A collimator C for limiting an irradiation area of the radiations is arranged between the radiation source 108 and the subject. The radiation imaging apparatuses D1 and D2 each include a radiation detection panel which includes a plurality of pixels arranged in a two-dimensional matrix and converts irradiated radiations into an image signal. The radiation imaging apparatuses D1 and D2 capture an image based on radiations transmitted through the object, i.e., subject. Direct conversion sensors for directly converting radiations into an electrical signal, such as a-Se, and indirect sensors using a scintillator and a photoelectric conversion element, such as CsI, can be used as sensors for converting the radiations into an electrical signal. The radiation imaging apparatuses D1 and D2 further perform analog-to-digital (A/D) conversion on the converted electrical signals to generate captured images serving as radiography data, and transfer the captured images to the radiography control unit 112.

In the radiation imaging system S illustrated in FIGS. 1A and 1B, a first radiation imaging apparatus D1 is arranged on the radiation source 108 side, i.e., radiation irradiation side of a second radiation imaging apparatus D2. The first radiation imaging apparatus D1 is arranged to spatially overlap with the second radiation imaging apparatus D2 when seen from the radiation irradiation side. As employed herein, "overlapping spatially" may refer to overlapping with a physical contact, or overlapping via a gap without a physical contact. The presence of the overlapping area enables image composition. In the area 120, some of structures of the radiation imaging apparatus D1 arranged on the radiation irradiation side are imaged by the second radiation imaging apparatus D2. This produces an area of lower image quality. The radiation imaging system S illustrated in FIG. 1 is a radiation imaging system including radiation imaging apparatuses that convert irradiated radiations transmitted through an object into image signals serving as partial images of the object, and obtains a radiation image of the object based on a plurality of image signals.

The plurality of radiation imaging apparatuses is held by a holding unit to be described below so that the radiation image is obtained at positions relatively shifted in a direction intersecting a direction in which one of the plurality of radiation imaging apparatuses adjoins another one of the radiation imaging apparatuses (arranged direction). As illustrated in FIG. 1B, the possible amounts of movement of the radiation imaging apparatuses D1 and D2 in a transverse direction of the radiation imaging system S, which is the intersecting direction, may desirably be such that a distance between the sides of effective imaging areas of the respective radiation imaging apparatuses D1 and D2 where radiation imaging can be performed is 5 cm or more. As employed herein, an effective imaging area refers to an area of the radiation detection panel corresponding to a pixel array including a plurality of pixels arranged in a two-dimensional matrix. In one embodiment, a length of the overlapping parts of the effective imaging areas in the transverse direction may desirably be 5 cm or more. While such a movable configuration can reduce the overlapping parts of the radiation imaging apparatuses D1 and D2, but it is possible to capture a wide range image at a time regardless of the widths of the radiation imaging apparatuses D1 and D2, for example, when a subject with a hump back is imaged from a side. The presence of the overlapping parts enables image composition. While all the plurality of radiation imaging apparatuses accommodated in the radiation imaging system S is described to be movable, one or some of the radiation imaging apparatuses may be fixed and the rest of the radiation imaging apparatuses may be configured to be movable. Three or more radiation imaging apparatuses may be included. The holding unit of the present radiation imaging system S holds the radiation imaging apparatuses movably in the direction intersecting the direction in which the positions to obtain the plurality of partial images are arranged. In other words, the holding unit of the present radiation imaging system S holds the radiation imaging apparatuses so that one of the plurality of partial images overlaps with another adjoining one of the partial images in the arranged direction, and the radiation image is obtained in positions relatively shifted in the direction intersecting the adjoining direction. A configuration of the radiation imaging system S will be described in detail below.

The radiation generation control unit 111 controls generation of radiations based on an imaging protocol according to control of the radiography control unit 112. More specifically, the radiation generation control unit 111 applies a voltage to the radiation source 108 to generate radiations according to an imaging condition (e.g., parameters such as a tube current, a tube voltage, and an irradiation time) corresponding to the imaging protocol.

The radiography control unit 112 collectively controls radiography processing based on an imaging protocol. The radiography control unit 112 performs image processing on captured images obtained from the radiation imaging system S. The image processing includes composition processing, correction processing, gradation processing, and frequency processing of a plurality of captured images from the radiation imaging apparatuses D1 and D2. The image processing of the radiography control unit 112 is performed by using image processing parameters according to the imaging protocol. The radiography control unit 112 can transmit the obtained captured images to an external apparatus such as the PACS 103 and the printer 105. If captured images are transmitted thereto, the PACS 103 stores the transmitted captured images with inspection information for identifying the captured images. For example, the inspection information may be an inspection ID or reception number given to an inspection order. The PACS 103 may store the inspection order in association with the captured images.

The display unit 113 displays information such as a system state to the operator. Examples of the display unit 113 may include a display monitor. For example, the display unit 113 can display an inspection order received from the RIS 102 or an inspection order generated by the operator of the radiography system 107. The operation unit 114 obtains instructions from the operator. Examples of the operation unit 114 may include a keyboard, a mouse, and various buttons. For example, the operator can input an instruction for image duplication to the radiography system 107 via the operation unit 114.

Figure 2A:
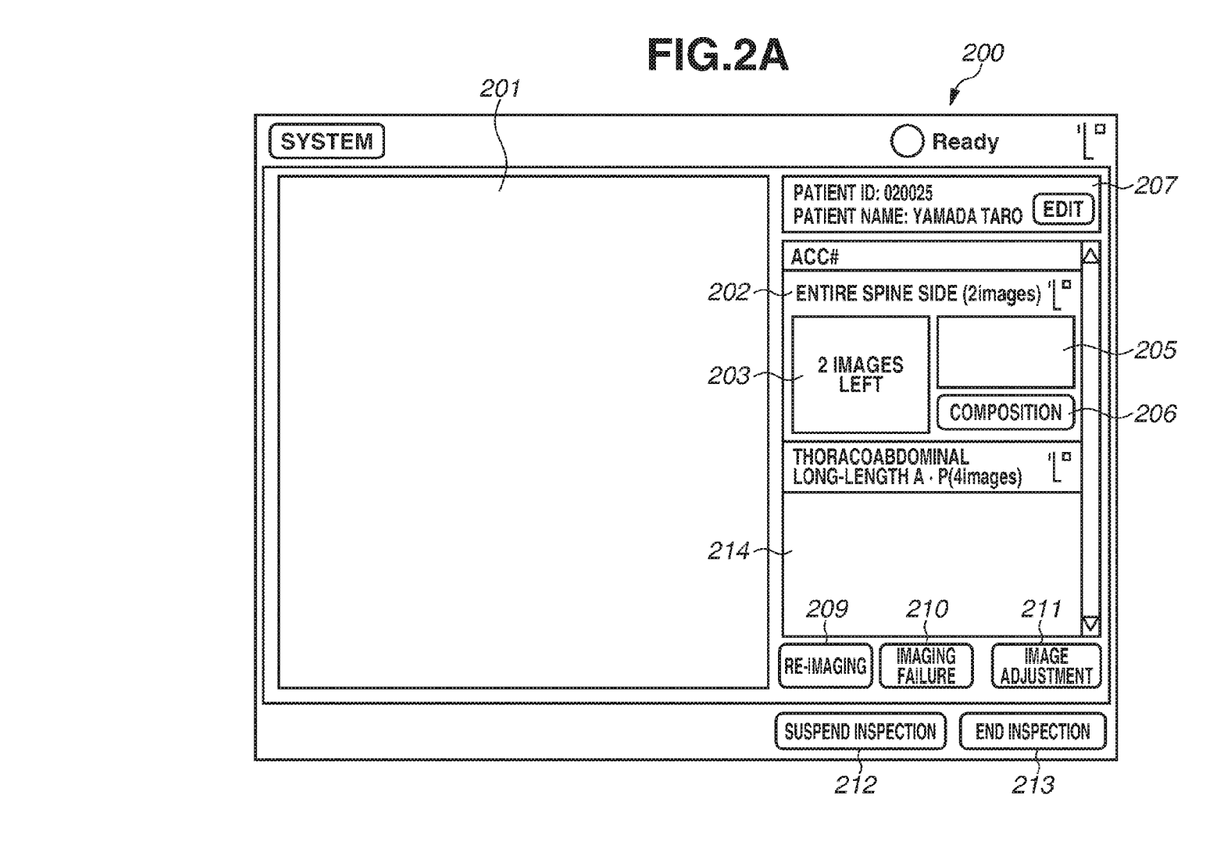
FIGS. 2A, 2B, and 2C are schematic diagrams illustrating generation of an obtained long image.
Figure 2B:
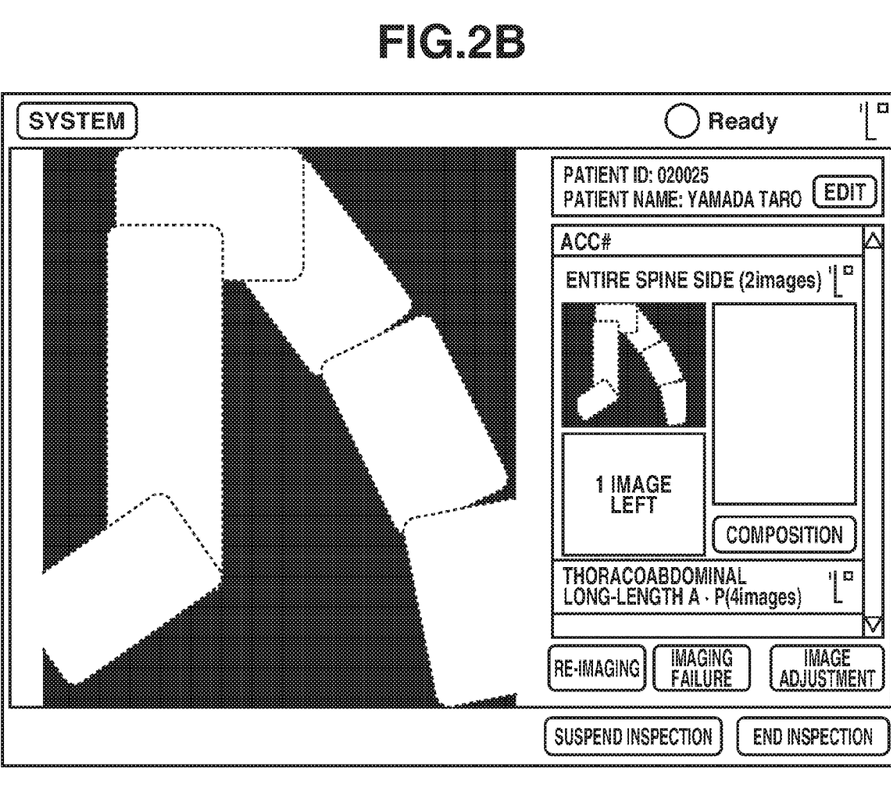
Figure 2C:
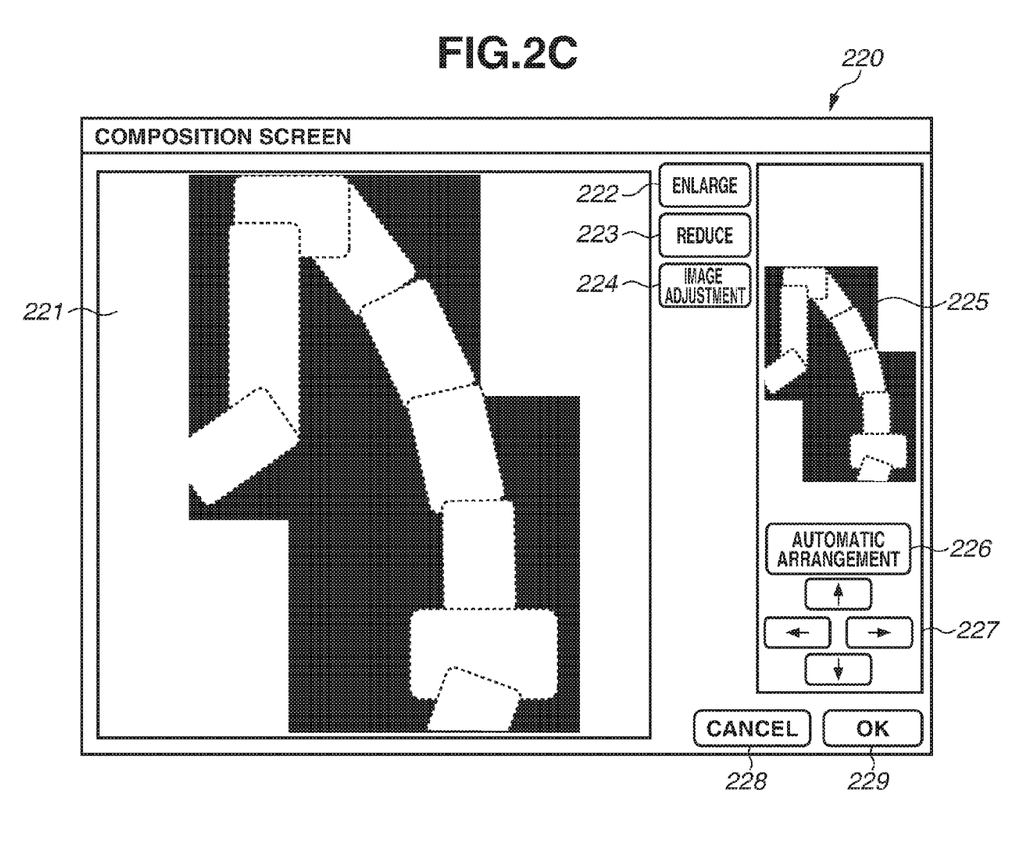

Next, generation of a long image (radiation image) obtained by the imaging of the radiation imaging system S illustrated in FIGS. 1A and 1B will be described with reference to 2A, 2B, and 2C. FIG. 2A illustrates an example of an imaging screen, which is displayed on the display unit 113. An imaging screen 200 includes an image display section 201 for displaying a captured image, a patient information display section 207 for confirming patient information, and an imaging protocol list display section 214 for displaying a list of imaging protocols. The imaging screen 200 further includes a re-imaging button 209 that facilitates re-imaging due to detection of the subject's body movement, an imaging failure button 210 for discarding an unnecessary captured image, and an image adjustment button 211 for transitioning to an image processing adjustment screen. The imaging screen 200 further includes a suspend inspection button 212 for suspending the inspection in process, and an end inspection button 212 for ending the inspection. When long-length imaging is performed, an imaging protocol display section 202 of the imaging protocol list display section 214 displays the protocol of the long-length imaging. The long-length imaging protocol display section 202 includes a thumbnail image display section 203 for displaying a thumbnail or thumbnails of a captured image or images, a composite image display section 205 for displaying a composite image, and a composition button 206 used for transitioning to a screen for generating a composite image. The thumbnail image display section 203 further includes a remaining image number display function for displaying the number of remaining images for the long-length imaging. The imaging screen 200 is in a state where a long-length imaging protocol for two-image capturing is selected. The number of remaining images to be captured is displayed to be two. Captured images will be displayed in the preview image display section 201 and the thumbnail image display section 203. Imaging is repeated until the number of captured images coincides with the total number of images to be captured. After the end of imaging up to the total number of images to be captured, the imaging screen 200 automatically transitions to display a composition screen 220. The imaging screen 200 may be set to transition to the composition screen 220 when the user presses the end inspection button 213. In such a case, the imaging screen 200 transitions like from FIG. 2B to FIG. 2C. FIG. 2C illustrates an example of a composite image. The composition screen 220 includes a composite image preview display section 221 for displaying a composite image, and a composite image thumbnail display section 225 for displaying a thumbnail of the composite image. The composition screen 220 includes an enlargement button 222 for enlarging the composite image, a reduction button 223 for reducing the composite image, an image adjustment button 224 for transitioning to a screen for performing various image adjustments, an automatic arrangement button 226 for automatically arranging the images to be composited, and up, down, left, and right buttons 227 for making fine adjustments to the arranged positions. The composition screen 220 further includes a cancel button 228 for closing the composition screen 220 without reflecting processing, and an OK button 229 for reflecting processing to generate a composite image and closing the composition screen 220. If the user makes adjustments on the composition screen 220 and presses the OK button 229, the composition processing is performed and the composite image is stored into an image storage unit (not illustrated). The radiography control unit 112 then notifies the radiation generation control unit 111 of the end of the long-length imaging. To composite images, positioning is performed on the overlapping area of the radiation imaging apparatuses D1 and D2 where the two images overlap. The positioning is performed through visual observation, matching of structure information by image analysis, and/or using markers to be described below. Alternatively, a positional shift amount detection unit such as a position sensor built in the radiation imaging system S may be used for positioning. A spread correction for making corrections from the center of irradiation corresponding to the position of the radiation source 108 may be performed. In such a case, corrections are made in the transverse direction, in which the width is wider than heretofore, in addition to the longitudinal direction of the long-length imaging in which the radiation imaging apparatuses D1 and D2 adjoin.

Figure 3:
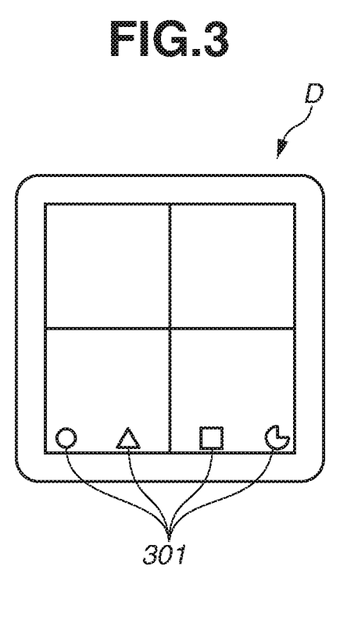
FIG. 3 is a schematic diagram illustrating an example of performing positioning.

Next, an example of performing positioning by using markers will be described with reference to FIG. 3. FIG. 3 illustrates an example in which the markers are arranged on the front side of the casing of a radiation imaging apparatus D. As illustrated in FIG. 3, by arranging markers 301 of different shapes, the positions of radiation imaging apparatus D can be identified even in a case where the radiation imaging apparatus D is shifted in a direction intersecting the direction in which the radiation imaging apparatuses D adjoin each other. FIG. 3 illustrates an example where the direction intersecting the adjoining direction is a direction orthogonal to the adjoining direction. To provide accurate measurement points for diagnosis, in one embodiment, an angular shift is to be suppressed at the time of image composition. Therefore, the width of the overlapping area may desirably be 5 cm or more. The distances between the markers may desirably set so as to include two markers in the overlapping area. The distances may desirably be smaller than or equal to ½ the width of the overlapping area. The radiation imaging system S may include a control unit for moving the marker positions into the overlapping area according to an amount of relative positional shift obtained by a position sensor built in the casing of the radiation imaging system S. The markers may be configured only to be able to identify the positions of images. For example, markers having the same shapes and different radiation transmittances may be used. In the present example, the radiation imaging apparatuses D are described to include the additional markers. Instead, structures of the radiation imaging apparatuses D may be used as characteristic portions based on which the positions of the images can be identified. Examples include corners, screws, and other component parts of the radiation imaging apparatuses D.

Figure 4A:
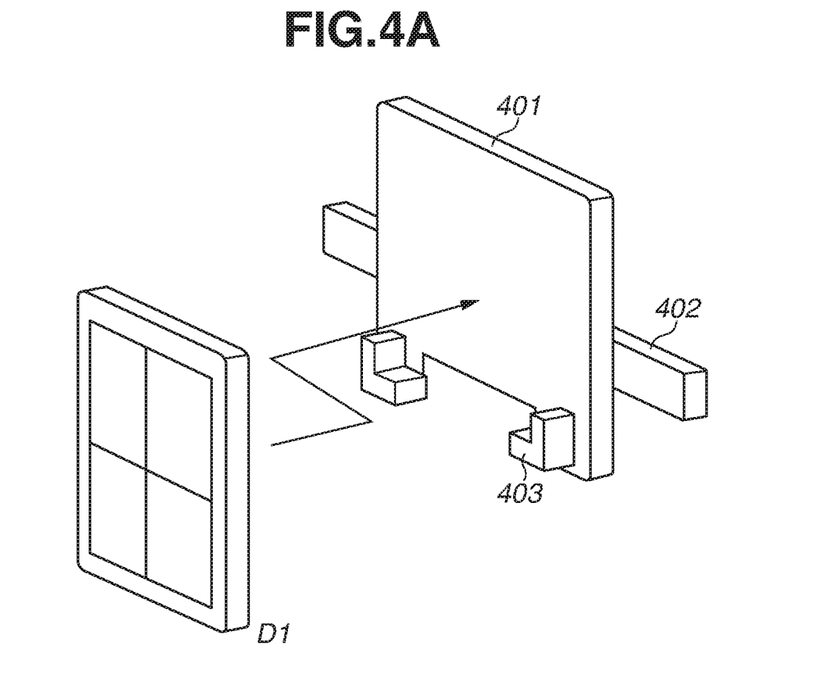
FIGS. 4A and 4B are schematic diagrams illustrating a holding unit of the radiation imaging system according to an exemplary embodiment of the present invention.
Figure 4B:
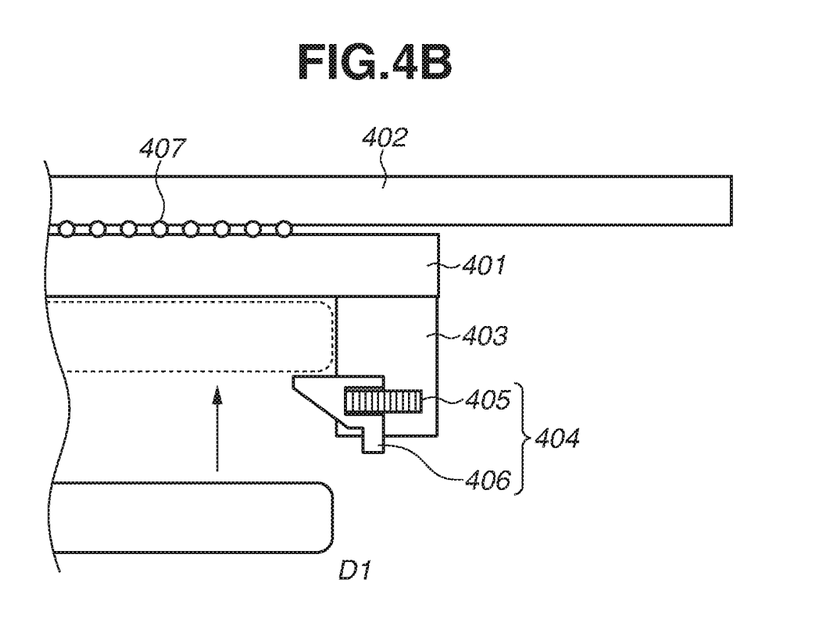

Next, the holding unit according to an exemplary embodiment of the present invention will be described in detail by using an example illustrated in FIGS. 4A and 4B. FIG. 4A is a schematic perspective view illustrating the holding unit that positions and holds a radiation imaging apparatus D in the system casing of the radiation imaging system S. FIG. 4B is a schematic sectional view of the holding unit as seen from above the radiation imaging system S. The radiation imaging system S includes the holding unit which includes a holding member 401, a movable member 402, and placement members 403. The holding member 401 is a plate-like member mechanically connected with the movable member 402 and the placement members 403. The holding member 401 supports the rear surface of the radiation imaging apparatus D, and movably positions and holds the radiation imaging apparatus D by using the movable member 402 and the placement members 403. The movable member 402 is configured to hold the holding member 401 so that a relative position of the holding member 401 can be moved in a direction intersecting the direction in which the radiation imaging apparatuses D adjoin. The placement members 403 are mechanically connected with and arranged on the holding member 401 so that the radiation imaging apparatus D is placed thereon at sides and corners of the radiation imaging apparatus D. The holding unit may further include a fixing member 404 for sandwiching the radiation imaging apparatus D. The fixing member 404 includes an elastic member 405 and a protruding member 406 so that the radiation imaging apparatus D can be sandwiched. The protruding member 406 of various forms capable of holding the radiation imaging apparatus D can be used. Examples include a claw-like shape and a ball-like shape. The elastic member 405 may be a spring or a rubber member. The protruding member 406 may be made of an elastic body such as rubber, and may be integrally formed with the elastic member 405. Such a fixing member 404 can prevent the radiation imaging apparatus D from falling from the holding unit, and allows easy attachment and detachment. The holding unit further includes a moving mechanism 407 for moving relative positions of the holding member 401 and the movable member 402. A bearing is used as the moving mechanism 407. The moving mechanism 407 allows the holding member 401 to slide over the movable member 402. A restriction member (not illustrated) for restricting movement to a predetermined position and/or a position regulation member (not illustrated) for regulating position may be provided on the movable member 402 to facilitate holding (positioning) the position of the radiation imaging apparatus D in the intersecting direction. With such a configuration, the holding unit can position and hold a plurality of radiation imaging apparatuses so that a radiation image is obtained in positions relatively shifted in the direction intersecting the direction in which one radiation imaging apparatus adjoins another radiation imaging apparatus.

Figure 5A:
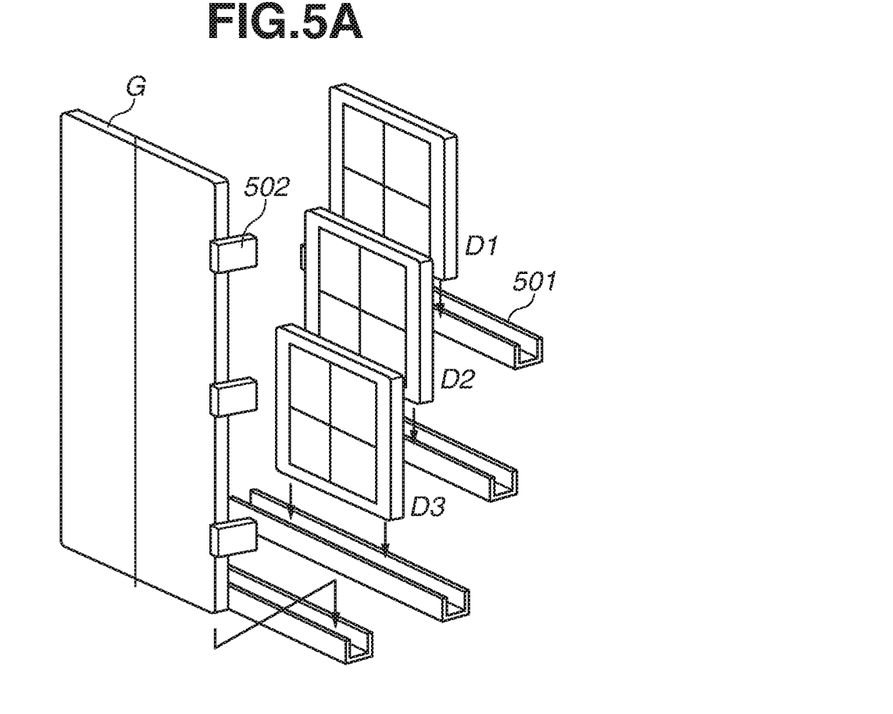
FIGS. 5A and 5B are schematic diagrams illustrating another example of the holding unit of the radiating imaging system according to an exemplary embodiment of the present invention.
Figure 5B:
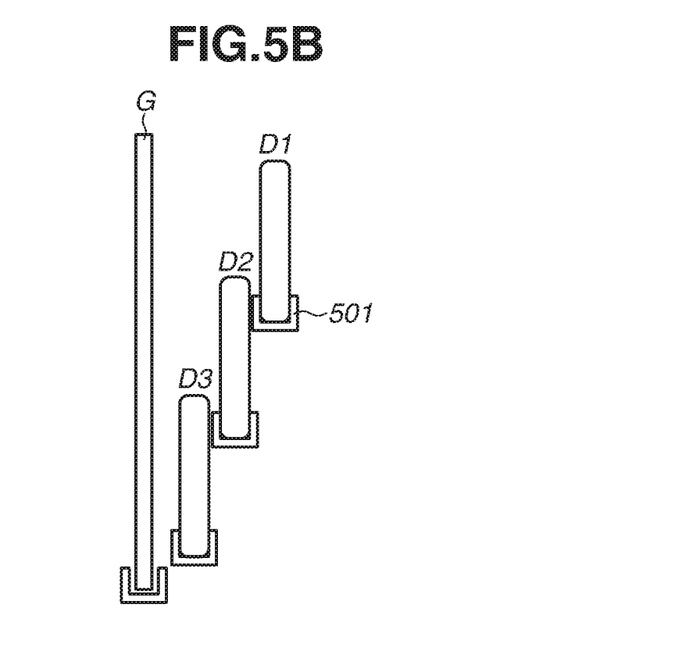

Next, another example of the holding unit according to an exemplary embodiment of the present invention will be described with reference to FIGS. 5A and 5B. FIG. 5A is a schematic perspective view illustrating another example of the holding unit. FIG. 5B is a schematic sectional view illustrating the example of the holding unit, viewed from a side of the radiation imaging system S. In the example illustrated in FIGS. 5A and 5B, rails 501 each having a groove for a radiation imaging apparatus D to be fitted into are used as the holding unit. The rails 501 hold the radiation imaging apparatuses D to be movable in a direction intersecting the adjoining direction. For example, a rail 501 is arranged below a radiation imaging apparatus D2 on a side opposite to the radiation irradiation side of a radiation imaging apparatus D3 which lies on the radiation irradiation side of the radiation imaging apparatus D2. Such an arrangement can minimize the appearance of the holding unit in an image, so that a favorable long image can be obtained. A restriction member (not illustrated) for restricting movement to a desired position and a position regulation member (not illustrated) for regulating position can be provided on each of the rails 501 to facilitate holding (positioning) the position of the radiation imaging apparatus D in the intersecting direction. A grid holding unit G for holding a grid for removing scattering rays may be arranged in front of the system casing of the radiation imaging system S. The grid holding unit G may also be held by a rail 501 to be movable in the intersecting direction. A stopper 502 for restricting the movement of the radiation imaging apparatus D may be arranged on a side surface of the grid holding unit G. Other examples of the holding unit may include a mechanism that movably holds the radiation imaging apparatus D with a configuration capable of expansion and contraction according to the movement of the radiation imaging apparatuses D, using a telescopic mechanism, a pantograph, or a multi-joint arm.

Figure 6:
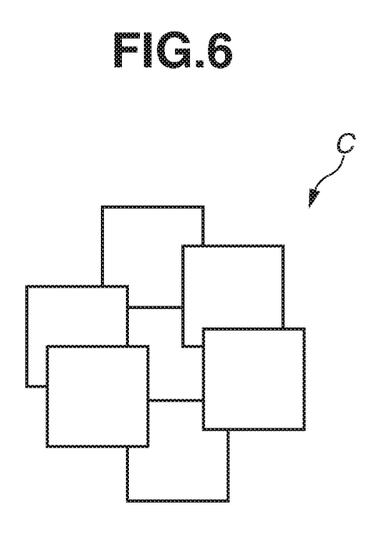
FIG. 6 is a schematic diagram illustrating a collimator suitable for a radiography system according to an exemplary embodiment of the present invention.

Next, the collimator C suitably used in the radiography system 107 using the radiation imaging system S according to an exemplary embodiment of the present invention will be described in detail with reference to FIG. 6. FIG. 6 is a schematic diagram illustrating an arrangement of the collimator C when the radiation imaging system S is seen from the radiation source 108. An ordinary collimator includes four radiation shielding plates to form a rectangular radiation irradiation area. Suppose that the radiation irradiation area of such a collimator is set to irradiate all the radiation imaging apparatuses D when imaging is performed with the radiation imaging apparatuses D shifted in the intersecting direction to each other. In such a case, areas where the radiation imaging apparatuses D are not located (areas not requiring radiation irradiation) can also be irradiated with the radiations. The collimator C of the present radiation imaging system S includes a plurality of radiation shielding plates to configure sides of the radiation irradiation area in the direction in which the plurality of radiation imaging apparatuses D adjoins. With such a configuration, the radiation irradiation area, in the direction in which the plurality of radiation imaging apparatuses D adjoins each other, can be shifted in a direction intersecting the adjoining direction. In the example illustrated in FIG. 6, to form a radiation irradiation area like the one in FIG. 1B, the collimator C includes a total of six radiation shielding plates, with two of the radiation shielding plates arranged in the direction in which the plurality of radiation imaging apparatuses D adjoins. The positions of the radiation shielding plates of the collimator C may be controlled by, for example, the radiography control unit 112 to move in an interlocking manner based on position information about the radiation imaging apparatuses D. The position information is supplied from the radiation imaging system S. Indexes for indicating the arranged positions of the radiation imaging apparatuses D according to movements of the respective radiation imaging apparatuses D may be provided in front of the radiation imaging system S, and the positions of the radiation shielding plates may be regulated according to the indexes. In the position adjustment before imaging, the radiography control unit 112 may display the positions of the radiation imaging apparatuses D and the radiation irradiation area formed by the collimator C on the display unit 113. This enables efficient long-length imaging.

Figure 7A:
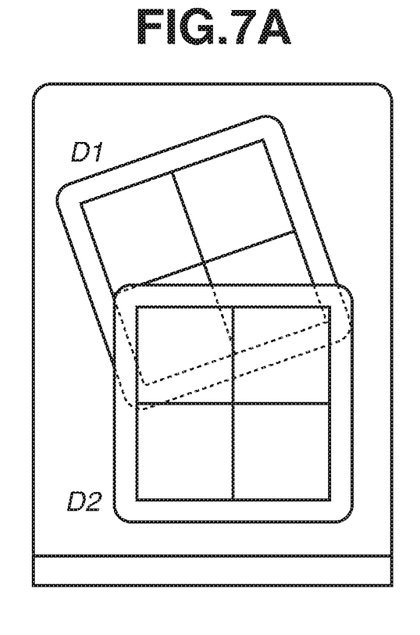
FIGS. 7A and 7B are schematic diagrams illustrating another example of the radiation imaging system according to an exemplary embodiment of the present invention.
Figure 7B:
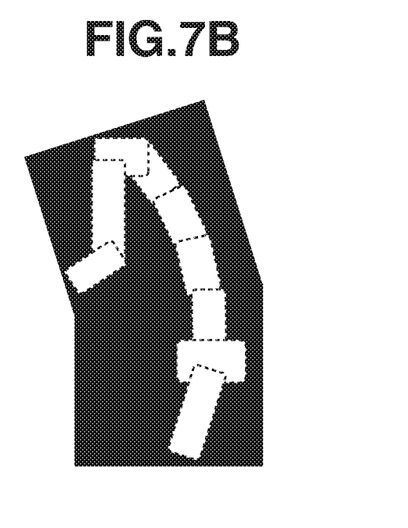

The holding unit for holding the radiation imaging apparatuses D at positions relatively shifted in a direction intersecting the direction in which one of the radiation imaging apparatuses D adjoins another adjoining one of the radiation imaging apparatuses D is not limited to the one that moves the one radiation imaging apparatus D in the intersecting direction with respect to another adjoining radiation imaging apparatus D. For example, as illustrated in FIGS. 7A and 7B, the holding unit may hold the radiation imaging apparatuses D so that the radiation imaging apparatuses D are relatively shifted in an intersecting direction by a positional change including rotation. FIG. 7A is a schematic diagram illustrating another example of the radiation imaging system S. FIG. 7B illustrates a radiation image obtained by the example. As illustrated in FIG. 7A, the holding unit may include a mechanism that can move the radiation imaging apparatus D1 to rotate by a desired angle with respect to the direction in which the radiation imaging apparatus D1 adjoins the radiation imaging apparatus D2. The mechanism of the holding unit may be able to make not only a rotational movement but also a linear movement.

Figure 8A:
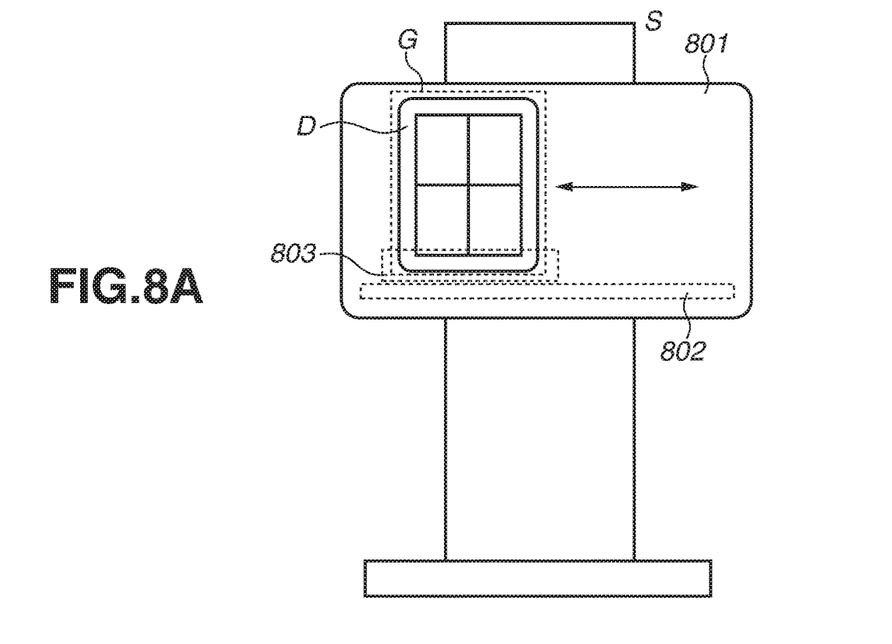
FIGS. 8A and 8B are schematic diagrams illustrating another example of the radiation imaging system according to an exemplary embodiment of the present invention.
Figure 8B:
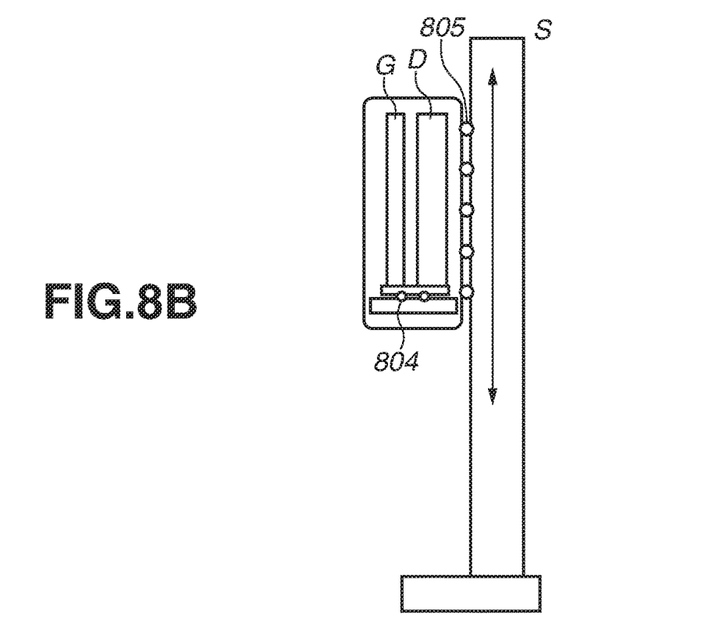

The present invention is not limited to a radiation imaging system that uses a holding unit for positioning and holding a plurality of radiation imaging apparatuses so that portions of the radiation imaging apparatuses spatially overlap with each other when seen from a radiation irradiation side. As illustrated in FIGS. 8A and 8B, an exemplary embodiment of the present invention may be applied to a radiation imaging system that obtains a radiation image based on an image signal obtained from a radiation imaging apparatus D a plurality of times by moving a holding unit holding the radiation imaging apparatus D in one direction. In such a case, the holding unit is moved so that the radiation image is obtained based on the image signal obtained from the radiation imaging apparatus D a plurality of times at positions relatively shifted in a direction intersecting the one direction. FIG. 8A is a front view illustrating a modification of the radiation imaging system according to an exemplary embodiment of the present invention. FIG. 8B is a side view thereof. The radiation imaging system illustrated in FIGS. 8A and 8B includes a holding unit that can change vertical and horizontal positions of the radiation imaging apparatus D and a grid holding unit G as indicated by the arrows. The radiation imaging system can obtain a radiation image based on an image signal obtained a plurality of times at different positions. The holding unit includes a holding member 801, a movable member 802, and a placement member 803. The holding member 801 is an accommodation box mechanically connected with the movable member 802. The holding member 801 accommodates the movable member 802 and the placement member 803, and movably positions and holds the radiation imaging apparatus D by using the movable member 802 and the placement member 803. The movable member 802 is configured to hold the holding member 801 to be movable in the direction intersecting the one direction. The placement member 803 is mechanically connected with and provided on the holding member 801 so that the radiation imaging apparatus D is placed thereon at sides and corners of the radiation imaging apparatus D. The holding unit further includes a moving mechanism 804 for moving relative positions of the movable member 802 and the placement member 803. The holding unit further includes a moving mechanism 805 for moving the holding member 801 in a vertical direction (longitudinal direction of long-length imaging). A partially-shifted long radiation image similar to that of the foregoing radiating imaging apparatuses D can thus be obtained. Since the imaging is performed a plurality of times, the holding unit, when moving the radiation imaging apparatus D in horizontal and vertical directions, controls the position of the radiation imaging apparatus D so that an overlapping area for connecting a plurality of images is included. The position of the radiation imaging apparatus D may be manually or automatically controlled by using light from the radiation source 108, the light indicating the radiation irradiation area, and/or based on the amount of movement and/or position of the radiation imaging apparatus D detected by the radiation imaging system itself or detected from a signal from the radiation imaging system. Since the radiation imaging apparatus D is to perform imaging a plurality of times, a positional deviation may occur due to body movement. However, a high degree of freedom of imaging in the transverse direction can be obtained with fewer radiation imaging apparatuses without sacrificing the imaging range in the longitudinal direction. It will be understood that in the description of FIGS. 1 to 7B, what are applicable to the radiation imaging system of FIG. 8 may be applied in a suitable manner.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-061690, filed Mar. 24, 2015, which is hereby incorporated by reference herein in its entirety.

What is claimed is:

1. A radiation imaging system comprising a plurality of radiation imaging apparatuses, each radiation imaging apparatus being configured to convert an irradiated radiation transmitted through an object into an image signal serving as a partial image of the object, and including a plurality of pixels arranged in a two-dimensional matrix, the radiation imaging system being configured to obtain a radiation image of the object by composing the partial images, the radiation imaging system comprising:
    a holding unit configured to hold the radiation imaging apparatus movably in a direction intersecting a direction in which the partial images are to be arranged as the radiation image so as to extend an imaging range toward the direction in which the radiation imaging apparatus is to be moved.

2. The radiation imaging system according to claim 1, comprising another radiation imaging apparatus,
    wherein the holding unit is configured to hold the plurality of radiation imaging apparatuses so that the plurality of radiation imaging apparatuses, as seen from a radiation irradiation side, spatially overlaps in the arranged direction, and the radiation image is obtained in positions where one of the plurality of radiation imaging apparatuses is relatively shifted from another adjoining one of the radiation imaging apparatuses in the intersecting direction.

3. The radiation imaging system according to claim 1, wherein the holding unit is configured to hold the radiation imaging apparatus so that one of the plurality of partial images overlaps with another adjoining one of the partial images in the arranged direction, and the radiation image is obtained based on the image signal obtained a plurality of times from the radiation imaging apparatus in positions relatively shifted in the intersecting direction while moving the radiation imaging apparatus in the arranged direction.

4. The radiation imaging system according to claim 1, wherein the intersecting direction is a direction orthogonal to the arranged direction.

5. The radiation imaging system according to claim 1, wherein the holding unit includes a placement member on which the radiation imaging apparatus is placed, a holding member mechanically connected with the placement member and configured to hold the radiation imaging apparatus, and a movable member configured to move the holding member in the intersecting direction.

6. The radiation imaging system according to claim 5, wherein the holding unit further includes a fixing member configured to sandwich the radiation imaging apparatus.

7. The radiation imaging system according to claim 1, wherein the holding unit includes a rail having a groove into which the radiation imaging apparatus is to be fitted.

8. The radiation imaging system according to claim 1, wherein the holding unit includes a mechanism configured to movably hold the radiation imaging apparatus with a configuration for expansion and contraction according to movement of the radiation imaging apparatus.

9. The radiation imaging system according to claim 1, wherein the holding unit further includes a restriction member configured to restrict movement of the radiation imaging apparatus to a desired position.

10. The radiation imaging system according to claim 1, wherein the holding unit further includes a position regulation member configured to regulate a position of the radiation imaging system.

11. The radiation imaging system according to claim 1, wherein the holding unit is configured to hold the radiation imaging apparatus to cause a relative shift in the intersecting direction by a positional change including rotation.

12. A radiography system comprising:
the radiation imaging system according to claim 1;
a radiation source configured to emit a radiation to the object; and
a collimator arranged between the radiation source and the radiation imaging system and configured to limit an irradiation area of the radiation,
wherein the collimator is configured to shift the irradiation area in the intersecting direction with respect to the arranged direction.

13. A radiation imaging system comprising a holding unit configured to hold a plurality of radiation imaging apparatuses so that the radiation imaging apparatuses spatially overlap with each other as seen from a radiation irradiation side, the radiation imaging apparatuses each including a plurality of pixels arranged in a two-dimensional matrix and being configured to convert an irradiated radiation into an image signal, the radiation imaging system being configured to obtain a radiation image based on the image signals from the respective plurality of radiation imaging apparatuses,
wherein the holding unit is configured to hold the plurality of radiation imaging apparatuses in positions relatively shifted in a direction intersecting a direction in which one of the plurality of radiation imaging apparatuses adjoins another one of the radiation imaging apparatuses so as to obtain the radiation image with an imaging range to be extended in the shifted direction.

14. A radiation imaging system comprising a holding unit configured to hold a radiation imaging apparatus, including a plurality of pixels arranged in a two-dimensional matrix and being configured to convert an irradiated radiation into the image signal serving as a partial image, to obtain a radiation image by composing the partial images each obtained one of a plurality of times from the radiation imaging apparatus while moving the radiation imaging apparatus in one direction,
wherein the holding unit is configured to move the radiation imaging apparatus in positions relatively shifted in a direction intersecting the one direction so as to obtain the radiation image with an imaging range to be extended in the shifted direction.

15. The radiation imaging system according to claim 14, wherein the holding unit includes a placement member on which the radiation imaging apparatus is placed, a holding member mechanically connected with the placement member and configured to hold the radiation imaging apparatus, and a movable member configured to move the holding member in the intersecting direction.

16. The radiation imaging system according to claim 15, wherein the holding unit further includes a fixing member configured to sandwich the radiation imaging apparatus.

17. The radiation imaging system according to claim 14, wherein the holding unit includes a rail having a groove into which the radiation imaging apparatus is to be fitted.

18. The radiation imaging system according to claim 14, wherein the holding unit includes a mechanism configured to movably hold the radiation imaging apparatus with a configuration for expansion and contraction according to movement of the radiation imaging apparatus.

19. The radiation imaging system according to claim 14, wherein the holding unit further includes a restriction member configured to restrict movement of the radiation imaging apparatus to a desired position.

20. The radiation imaging system according to claim 14, wherein the holding unit further includes a position regulation member configured to regulate a position of the radiation imaging system.

* * * * *